(12) United States Patent
Arora

(10) Patent No.: US 9,615,758 B2
(45) Date of Patent: Apr. 11, 2017

(54) CONTRIBUTION OF OXIDATIVE STRESS TO AF ELECTROGRAMS

(71) Applicant: NORTHWESTERN UNIVERSITY, Evanston, IL (US)

(72) Inventor: Rishi Arora, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 14/169,751

(22) Filed: Jan. 31, 2014

(65) Prior Publication Data

US 2014/0221861 A1 Aug. 7, 2014

Related U.S. Application Data

(60) Provisional application No. 61/759,757, filed on Feb. 1, 2013.

(51) Int. Cl.
| | | |
|---|---|---|
| A61B 5/04 | (2006.01) | |
| A61B 5/046 | (2006.01) | |
| A61B 5/00 | (2006.01) | |
| A61K 48/00 | (2006.01) | |
| A61B 18/14 | (2006.01) | |
| A61B 18/00 | (2006.01) | |

(52) U.S. Cl.
CPC ......... *A61B 5/04014* (2013.01); *A61B 5/046* (2013.01); *A61B 5/4839* (2013.01); *A61B 18/1492* (2013.01); *A61K 48/0058* (2013.01); *A61B 2018/00351* (2013.01); *A61B 2018/00577* (2013.01); *A61B 2018/00839* (2013.01); *A61B 2018/00904* (2013.01)

(58) Field of Classification Search
USPC ......................................................... 600/518
See application file for complete search history.

(56) References Cited

U.S. PATENT DOCUMENTS

| | | | |
|---|---|---|---|
| 2008/0075666 A1* | 3/2008 | Dudley, Jr. ............ | A61K 31/40 424/9.2 |
| 2013/0324869 A1 | 12/2013 | Arora et al. | |
| 2014/0037545 A1 | 2/2014 | Arora | |

FOREIGN PATENT DOCUMENTS

| | | |
|---|---|---|
| WO | 2006060366 A2 | 6/2006 |
| WO | 2008035070 A2 | 3/2008 |

OTHER PUBLICATIONS

Arora et al., "Arrhythmogenic Substrate of the Pulmonary Veins Assessed by High-Resolution Optical Mapping," Circulation 107(13):1816-1821 (2003).

(Continued)

*Primary Examiner* — Nicole F Johnson
(74) *Attorney, Agent, or Firm* — Klintworth & Rozenblat IP LLC

(57) ABSTRACT

The invention relates generally to methods of detecting reactive oxygen species (ROS) in cardiac tissue and treatment modalities for ablating ROS-associated tissue in cardiac disease. The methods rely upon targeting ROS-associated cardiac tissue for ablation and/or gene therapy in a subject using analytical tools based upon a plurality of recorded atrial EGMs for a tissue to assess ROS content and underlying AF organization as a function of ROS blockade conditions.

11 Claims, 16 Drawing Sheets

(56) References Cited

OTHER PUBLICATIONS

Carnes et al., "Ascorbate Attenuates Atrial Pacing-Induced Peroxynitrite Formation and Electrical Remodeling and Decreases the Incidence of Postoperative Atrial Fibrillation," Circ. Res. 89:e32-e38 (2001).
Carnes et al., "Atrial Glutathione Content, Calcium Current, and Contractility," J. Biol. Chem. 282(38):28061-28073 (2007).
Cave et al. "NADPH oxidases in cardiovascular health and disease," Antioxid. Redox. Signal. 8:691-728 (2006).
Dudley et al., "Atrial fibrillation increases production of superoxide by the left atrium and left atrial appendage: role of the NADPH and xanthine oxidases," Circulation 112:1266-1273 (2005).
Efimov et al., "Optical Imaging of the Heart," Circ. Res. 95:21-33 (2004).
Filgueiras-Rama et al., "Long-Term Frequency Gradients During Persistent Atrial Fibrillation in Sheep Are Associated With Stable Sources in the Left Atrium," Circ. Arrhythm. Electrophysiol. 5:1160-1167 (2012).
Hayward et al., "Pulmonary vein isolation with complex fractionated atrial electrogram ablation for paroxysmal and nonparoxysmal atrial fibrillation: A meta-analysis," Heart Rhythm. 8:994-1000 (2011).
Hori et al., "Oxidative stress and left ventricular remodelling after myocardial infarction," Cardiovascular Research 81:457-464 (2009).
Katra et al., "Cellular Mechanism of Calcium-Mediated Triggered Activity in the Heart," Circ. Res. 96:535-542 (2005).
Kim et al., "A myocardial Nox2 containing NAD(P)H oxidase contributes to oxidative stress in human atrial fibrillation," Circ Res. 97:629-636 (2005).
Koduri et al., "Contribution of Fibrosis and the Autonomic Nervous System to Atrial Fibrillation Electrograms in Heart Failure," Circ. Arrhythm. Electrophysiol. 5(4):640-649 (2012).
Kohlhaas et al., "Interplay of defective excitation-contraction coupling, energy starvation, and oxidative stress in heart failure," Trends Cardiovasc. Med. 21:69-73 (2011).
Kong et al., "Intramural optical mapping of Vm and Cai2+ during long-duration ventricular fibrillation in canine hearts," Am. J. Physiol. Heart Circ. Physiol. 302:H1294-H1305 (2012).
Kuroda et al., "NADPH oxidase 4 (Nox4) is a major source of oxidative stress in the failing heart," Proc. Natl. Acad. Sci., USA 107:15565-15570 (2010).
Maejima et al., "Regulation of myocardial growth and death by NADPH oxidase," J. Mol. Cell. Cardiol. 50:408-416 (2011).
Maulik et al., "Oxidative stress and cardiac hypertrophy: a review," Toxicol. Mech. Methods 22:359-366 (2012).
Mihm et al., "Impaired myofibrillar energetics and oxidative injury during human atrial fibrillation," Circulation 104:174-180 (2001).
Murdoch et al., "NADPH oxidase-dependent redox signalling in cardiac hypertrophy, remodelling and failure," Cardiovasc. Res. 71:208-215 (2006).
Nabeebaccus A, Zhang M, Shah AM. "NADPH oxidases and cardiac remodelling," Heart Fail. Rev. 16:5-12 (2011).
Nademanee et al., "A new approach for catheter ablation of atrial fibrillation: mapping of the electrophysiologic substrate," J. Am. Coll. Cardiol. 43:2044-2053 (2004).
Reilly et al., "Atrial sources of reactive oxygen species vary with the duration and substrate of atrial fibrillation: Implications for the antiarrhythmic effect of statins," Circulation 124:1107-1117 (2011).
Shimano et al., "Reactive oxidative metabolites are associates with atrial conduction disturbance in patients with atrial fibrillation," Heart Rhythm 6(7):935-936 (2009).
Tsai et al., "NADPH oxidase-derived superoxide anion-induced apoptosis is mediated via the JNK-dependent activation of NF-kappaB in cardiomyocytes exposed to high glucose," J. Cell. Physiol. 227:1347-1357 (2012).
Wasserstrom et al., "Variability in Timing of Spontaneous Calcium Release in the Intact Rat Heart is Determined by the Time Course of Sarcoplasmic Reticulum Calcium Load," Circ. Res. 107(9):1117-1126 (2010).
Zhang et al., "NADPH oxidase-4 mediates protection against chronic load-induced stress in mouse hearts by enhancing angiogenesis," Proc. Natl. Acad. Sci., USA 107:18121-18126 (2010).
International Search Report and Written Opinion from PCT/US2014/014228 dated Jun. 19, 2014, 10 pages.

* cited by examiner

CONTRIBUTION OF OXIDATIVE STRESS TO AF ELECTROGRAMS

CROSS-REFERENCE TO RELATED APPLICATIONS

This application claims benefit of priority under 35 U.S.C. 119 to U.S. provisional patent application Ser. No. 61/759,757 filed Feb. 1, 2013, and entitled "CONTRIBUTION OF OXIDATIVE STRESS TO AF ELECTROGRAMS," the contents of which is herein incorporated by reference in its entirety.

STATEMENT REGARDING FEDERALLY SPONSORED RESEARCH OR DEVELOPMENT

This invention was made with government support under R01HL093490 awarded by the National Institutes of Health. The government has certain rights in the invention.

FIELD OF THE INVENTION

The invention relates generally to methods of detecting reactive oxygen species (ROS) in cardiac tissue and treatment modalities for ablating ROS-associated tissue in cardiac disease.

BACKGROUND

Atrial fibrillation (AF) is a complex arrhythmia with a variety of underlying molecular and structural mechanisms contributing to a vulnerable AF substrate. The complexity of AF substrate seems to be reflected in the characteristics of AF electrograms (EGMs), with AF EGM morphology in paroxysmal AF being different than in more persistent AF. However, the precise structural and functional mechanisms that lead to the formation of AF EGMs have not been well elucidated. The need for a better understanding of the mechanisms underlying AF EGM formation is heightened by several recent descriptions of regions of high-frequency activity during AF called complex fractionated atrial EGMs (CFAEs) (Nademanee K, McKenzie J, Kosar E, et al. A new approach for catheter ablation of atrial fibrillation: mapping of the electrophysiologic substrate." *J. Am. Coll. Cardiol.* 43:2044-53 (2004)). Several recent reports suggest that ablation of CFAEs seems to increase AF ablation success (Hayward R M, Upadhyay G A, Mela T et al. "Pulmonary vein isolation with complex fractionated atrial electrogram ablation for paroxysmal and nonparoxysmal atrial fibrillation: A meta-analysis," *Heart Rhythm.* 8:994-1000 (2011)).

In the setting of structural heart disease, specifically heart failure (HF), a variety of mechanisms (for example, changes in ion-channel expression and gap junction distribution, inflammation, oxidative stress, and a variety of structural changes) are thought to contribute to the creation of a vulnerable AF substrate.

Oxidative stress is attributed to oxygen derivatives with instabilities and increased reactivity, $O_2^-$, $H_2O_2$, and $OH^-$, that are generically categorized as "reactive oxygen species" (ROS) (Maejima Y, Kuroda J, Matsushima S, Ago T, Sadoshima J. "Regulation of myocardial growth and death by NADPH oxidase," *J. Mol. Cell. Cardiol.* 50:408-16 (2011). While ROS at low doses mediates physiological functions such as growth, differentiation, and metabolism (id.), excess ROS damages DNA, protein and lipids, and causes cell death in cardiomyocytes (id.). A wealth of research data points to increased oxidative stress as a key driver of the cardiac remodeling caused by chronic pressure overload, loss of functional myocardial tissue, or AF (Kohlhaas M, Maack C. "Interplay of defective excitation-contraction coupling, energy starvation, and oxidative stress in heart failure." *Trends Cardiovasc. Med.* 21:69-73 (2011); Maulik S K, Kumar S. "Oxidative stress and cardiac hypertrophy: a review," *Toxicol. Mech. Methods* 22:359-66 (2012)). Chronic ROS elevation also activates a variety of signaling pathways such as the TGF-β1 and MAP kinase subfamilies (Hori M, Nishida K. "Oxidative stress and left ventricular remodelling after myocardial infarction," *Cardiovascular Research* 81:457-64 (2009)), including ERK, JNK (Tsai K H. Wang W J. Lin C W, et al. "NADPH oxidase-derived superoxide anion-induced apoptosis is mediated via the JNK-dependent activation of NF-kappaB in cardiomyocytes exposed to high glucose," *J. Cell. Physiol.* 227:1347-57 (2012)) and p38-kinase; these pathways are important in the creation of structural changes in the heart (for example, fibrosis).

Recent evidence indicates that oxidative stress also contributes to structural and electrical remodeling in AF. Significant oxidative damage occurs in appendages of AF patients undergoing the Maze procedure (Mihm M J, Yu F, Carnes C A et al. "Impaired myofibrillar energetics and oxidative injury during human atrial fibrillation," Circulation 104:174-80 (2001). Dogs with sustained AF were shown to have an increase in protein nitration, suggesting enhanced oxidative stress (Carnes C A, Janssen P M, Ruehr M L, et al. "Atrial glutathione content, calcium current, and contractility," *J. Biol. Chem.* 282:28063-73 (2007); Carnes C A, Chung M K, Nakayama T, et al. "Ascorbate attenuates atrial pacing-induced peroxynitrite formation and electrical remodeling and decreases the incidence of postoperative atrial fibrillation" *Circ. Res.* 89:E32-8 (2001)). In AF induced by rapid atrial pacing, there was an increase in $O_2^-$ production and NADPH oxidase and xanthine oxidase activity in the LA (Dudley S C, Jr., Hoch N E, McCann L A et al. "Atrial fibrillation increases production of superoxide by the left atrium and left atrial appendage: role of the NADPH and xanthine oxidases," *Circulation* 112:1266-73 (2005)). NADPH oxidase (NOX2) is a major source of atrial ROS in patients with AF (Kim Y M, Guzik T J, Zhang Y H et al. "A myocardial Nox2 containing NAD(P)H oxidase contributes to oxidative stress in human atrial fibrillation. *Circ Res.* 97:629-36 (2005)). More recently, atrial sources of ROS have been shown to vary with the duration and substrate of AF, with NADPH oxidase being elevated early in AF and with mitochondrial oxidases and uncoupled NOS being noted in long standing AF (Reilly S N, Jayaram R, Nahar K et al. "Atrial sources of reactive oxygen species vary with the duration and substrate of atrial fibrillation: implications for the antiarrhythmic effect of statins" *Circulation* 124: 1107-17 (2011)).

ROS are generated within cells by the mitochondrial electron transport chain, the xanthine oxidase/dehydrogenase system, 'uncoupled' nitric oxide synthases (NOSs), cytochrome P450 and NADPH oxidases. The NADPH oxidase enzyme family are a major source of cardiovascular ROS (Murdoch C E, Zhang M, Cave A C, Shah A M. "NADPH oxidase-dependent redox signalling in cardiac hypertrophy, remodelling and failure," *Cardiovasc. Res.* 71:208-15 (2006); Cave A C, Brewer A C, Narayanapanicker A, et al. "NADPH oxidases in cardiovascular health and disease," *Antioxid. Redox. Signal.* 8:691-728 (2006)), with NOX2 being the dominant NADPH isoform in HF (Maejima Y, Kuroda J, Matsushima S, Ago T, Sadoshima J. "Regulation of myocardial growth and death by NADPH oxidase,"

J. Mol. Cell. Cardiol. 2011; Murdoch C E, Zhang M, Cave A C, Shah A M. "NADPH oxidase-dependent redox signalling in cardiac hypertrophy, remodelling and failure," *Cardiovasc. Res.* 71:208-15 (2006); Cave A C, Brewer A C, Narayanapanicker A et al. "NADPH oxidases in cardiovascular health and disease," *Antioxid. Redox. Signal.* 8:691-728 (2006)). However, more recent studies indicate that NOX4 in mitochondria plays an essential role in mediating oxidative stress during pressure overload-induced cardiac hypertrophy (Kuroda J, Ago T, Matsushima S, Zhai P, Schneider M D, Sadoshima J. "NADPH oxidase 4 (Nox4) is a major source of oxidative stress in the failing heart," *Proc. Natl. Acad. Sci., USA* 107:15565-70 (2010); Nabeebaccus A, Zhang M, Shah A M. "NADPH oxidases and cardiac remodelling," *Heart Fail. Rev.* 16:5-12 (2011); Zhang M, Brewer A C, Schroder K et al. "NADPH oxidase-4 mediates protection against chronic load-induced stress in mouse hearts by enhancing angiogenesis," *Proc. Natl. Acad. Sci., USA* 107:18121-6 (2010)).

Of the mechanistic changes that occur in the HF atrium, the generation of reactive oxygen species (ROS) is considered to be especially important in creating conditions conducive to the genesis and maintenance of AF. Yet fundamental information remains lacking about how best to detect ROS-enriched tissues or ROS-damaged tissues ("ROS-associated tissues") in AF EGM and how that information can be used to perform directed ablation of ROS-associated tissue to improve AF ablation success.

BRIEF SUMMARY

In a first respect, a method of targeting a region having reactive oxygen species-associated (ROS-associated) cardiac tissue for ablation in a subject is provided. The method can include several steps. The first step includes performing at least one EGM analysis of a plurality of recorded atrial EGMs for a site in the region suspected of having ROS-associated cardiac tissue. The second step includes determining one or more correlations of at least one AF EGM characteristic to a region having ROS-associated cardiac tissue from the plurality of recorded atrial EGMs for the site. The third step includes determining a first outcome of executing the second step and a second outcome of executing the second step for the site based upon the one or more correlations of at least one AF EGM characteristic to a region having ROS-associated cardiac tissue. The first outcome triggers a first decision to avoid ablation of the analysis region and the second outcome triggers a second decision to perform ablation of the analysis region of the site.

In a second respect, a method of targeting reactive oxygen species-associated (ROS-associated) cardiac tissue for ablation in a subject is provided. The method includes several steps. A first step includes performing at least one EGM analysis of a plurality of recorded atrial EGMs for a site in a region suspected of having ROS-associated cardiac tissue. The second step includes assessing the plurality of EGMs before or after ROS blockade. The third step includes determining a first outcome of executing the second step and a second outcome of executing the second step for the site based upon the one or more significant changes in EGM characteristics with ROS blockade. The first outcome triggers a first decision to avoid ablation of the analysis region and the second outcome triggers a second decision to perform ablation of the analysis region of the site.

In a third respect, computer program product is provided. The computer program product includes a computer readable medium having computer readable program code for targeting reactive oxygen species-associated (ROS-associated) cardiac tissue for ablation in a subject. The computer readable program code includes the several steps. The first step is performing at least one EGM analysis of a plurality of recorded atrial EGMs for a tissue before and after ROS blockade. The second step includes executing the following sets of instructions: (i) determining one or more correlations of at least one AF EGM characteristic to a region having (ROS-associated) cardiac tissue from the plurality of recorded atrial EGMs for the tissue; and (ii) determining a first outcome of executing step (b)(i) and a second outcome of executing step (b)(i) for the tissue based upon the one or more significant changes in EGM characteristics with ROS blockade for step (a)(ii). The first outcome triggers a first decision to avoid ablation of the analysis region and the second outcome triggers a second decision to perform ablation of the analysis region of the tissue.

In a fourth respect, a kit is provided. The kit includes (a) a computer program product as disclosed above; and (b) instructions.

In a fifth respect, method of reducing reactive oxygen species-associated (ROS-associated) cardiac tissue in a subject is provided. The method can include several steps. One step is providing an isolated therapeutic DNA. In one aspect, the therapeutic DNA includes a dominant negative TGF-β R2 cDNA expression vector that encodes and expresses dominant negative TGF-β R2 mRNA and protein in vivo. In another aspect, the therapeutic DNA includes a NOX2 shRNA transgene expression vector that encodes and expresses NOX2 shRNA in vivo. A second step includes administering the isolated therapeutic DNA to myocardial tissue of the subject. A third step includes an executing step that includes assessing ROS-associated cardiac tissue status of plurality of recorded atrial EGMs for a region of the myocardial tissue after administration of the therapeutic DNA. A fourth step includes determining a first outcome of executing step and a second outcome of executing step for a region based upon the one or more continued significant changes in EGM characteristics with administration of the therapeutic DNA. The first outcome triggers a first decision to forego therapy of the analysis and the second outcome triggers a second decision to perform therapy of the analysis region of the tissue.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

Figure 1:
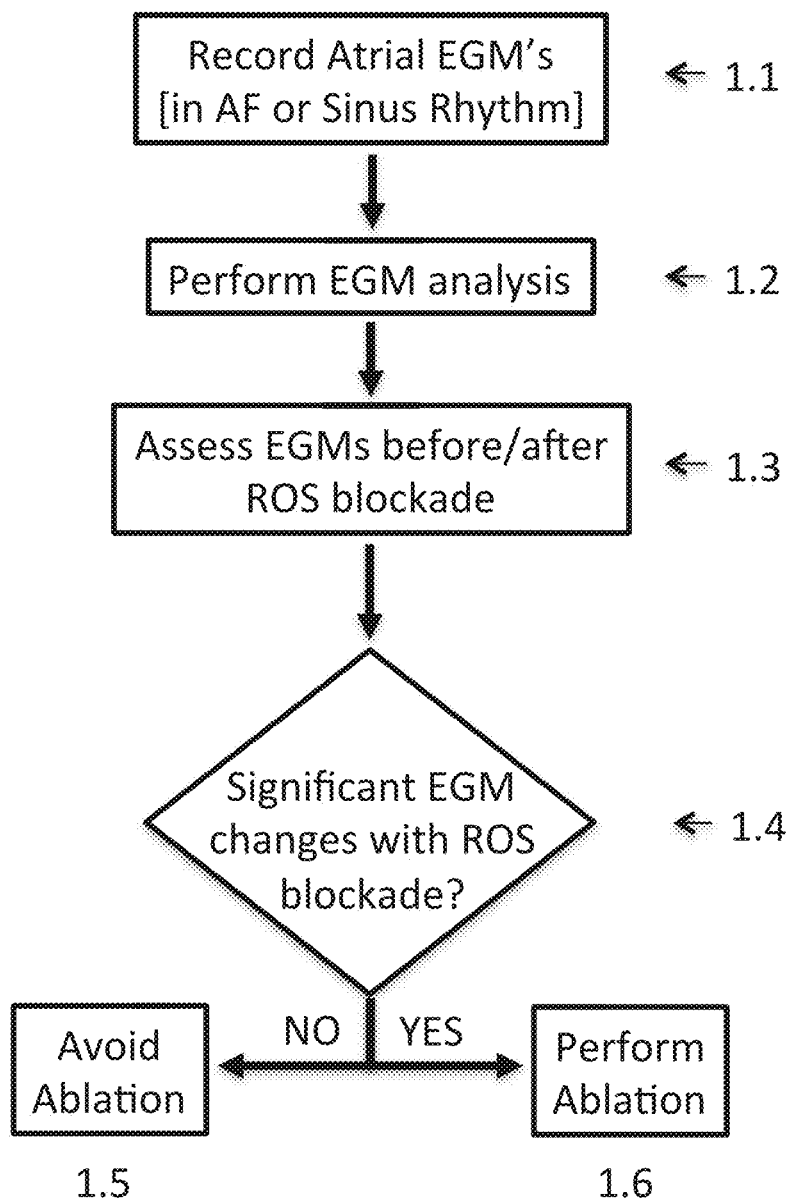
FIG. 1 depicts a flow-diagram for one preferred embodiment illustrating an analysis modality method for targeting ROS-associated cardiac tissue for treatment based upon analysis of atrial EGM's.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "reactive oxygen species-associated cardiac tissue" (ROS-associated cardiac tissue) is cardiac tissue having an increased level of ROS content than present in normal cardiac tissue, or AF cardiac tissue displaying altered EGM characteristics in response to an oxidase inhibitor, or cardiac tissue having suffered ROS-mediated damage.

Robust clinical diagnostic algorithms and methods are disclosed that enable use of Atrial fibrillation (AF) electrograms (EGMs) to detect specific AF mechanisms pertaining to reactive oxygen species (ROS) underlying AF in the context of congestive heart failure (CHF). The algorithms and methods of their use derive from novel systematic comparison of ROS-associated activity (significant EGM changes following ROS blockade) and the characteristics of overlying AF EGMs. The generated AF EGMs can be used to detect regions of ROS-associated cardiac tissue in the HF atrium. The decision end-point for the algorithms corresponds to whether specific sites should be subject to ablation therapy. The resolution of the AF EGM's, when coupled to the application of the algorithms enable increased success in performing highly precise substrate-guided ablation for HF.

Contribution of ROS to AF EGMs

The correlation between AF EGM characteristics and the underlying quantity and distribution of ROS-associated cardiac tissue was systematically assessed. Using a variety of time and frequency domain measures, the signal characteristics of AF EGMs in the setting of HF (where ROS-associated cardiac tissue is known to be a key contributor to the genesis and maintenance of AF) and compared these with AF EGMs in normal hearts (where AF was induced by vagal stimulation) were examined.

Though the details are presented in the Examples, the findings can be summarized as follows:

(1) AF EGMs in HF are very sensitive to acute blockade of NADPH oxidase and mitochondrial ROS;

(2) AF EGM organization in response to ROS blockade closely correlates with the amount of $O^{2-}$ in underlying tissue;

(3) a significant number of AF EGMs in HF and RAP are sensitive to ROS blockade, with 'highly responsive' EGMs overlying regions of high $O^{2-}$ levels;

(4) gene constructs targeted to TGF-β/NOX-2 can effectively inhibit ROS production in the atrium;

(5) EGM-guided gene injection in the atrium is feasible and robust, thereby providing reduction in ROS-associated cardiac tissue at the site of injection.

AF EGMs were systematically characterized in pacing-induced HF where ROS is thought to be a dominant mechanism underlying AF. ROS-generated EGM content is significantly different in normal versus HF atria. The strong correlation between the amount of ROS-associated cardiac tissue and the time and frequency domain measures of AF EGMs in HF reveals that ROS contributes to AF EGM characteristics. Patients with AF, worsening structural heart disease appears to contribute not only to the increasing chronicity of AF but also to AF EGM content.

EGM differences between HF and normal hearts can provide valuable insight into the patho-physiologic mechanisms underlying AF and may be of potential clinical significance in patients with AF undergoing AF ablation. It is well known that success rates of ablation procedures decrease in patients with permanent AF (compared with paroxysmal AF), at least, in part, because of the presence of structural heart disease in these patients.

The addition of EGM-guided ablation (for example, CFAE ablation) increases long-term success of these procedures. The increased regularity of EGMs (indicated by increased OI in HF) in the presence of slower activation rates (indicated by lower DFs and higher FIs) in HF indicates the presence of regions of underlying ROS-associated tissue. An enhanced ability to identify ROS-associated tissue (by real-time AF EGM analysis) allows for a greater precision in the placement of linear ablation lesions in the atrium.

Thus, one embodiment concerns a method of targeting ROS-associated cardiac tissue for ablation in a subject. The method includes recording an Atrial EGM from a subject (FIG. 1; 1.1). The subject is preferably a mammal; most preferably, the subject is a human. The subject is preferably a patient in need of monitoring cardiovascular disease; more preferably, the subject is a patient in need of preventative treatments for stroke or congestive heart failure, in particular, where such conditions are attributed to atrial fibrillation (AF); most preferably, the subject is a patient in need of monitoring sustained arrhythmia, such as atrial fibrillation (AF).

The Atrial EGM is preferably recorded in AF or in sinus rhythm. The recording is preferably obtained by standard procedures well known in the art.

Once obtained, an analysis of the EGM is performed using one or more analytical subroutines (FIG. 1; 1.2). EGM analysis can be performed with any analytical subroutine and the invention is not limited by the type of analytical subroutine employed. Highly preferred analytical subroutines include at least one member selected from the group consisting of dominant frequency analysis (DF), organizational index analysis (OI), fractional interval analysis (FI) and Shannon Entropy analysis (ShEn). The analysis of the EGM can be done on-line (for example, in real-time) or off-line (for example, using previously acquired EGM data provided in a readable computer media).

The analysis of the EGM can be performed preferably in accordance with one or more of the aforementioned analytical subroutines permits identification of one or more correlations of at least one AF EGM characteristic to a region having ROS-associated cardiac tissue. More preferably, one or more aforementioned analytical subroutines permits identification of one or more correlations of at least two AF EGM characteristics to a region having ROS-associated cardiac tissue. Most preferably, one or more aforementioned analytical subroutines permits identification of one or more correlations of three AF EGM characteristics to a regions having ROS-associated cardiac tissue.

Preferred correlations include one or more of the following: (i) mean DF negatively correlates with percentage $O^{2-}$; mean FI positively correlates with percentage $O^{2-}$; and mean OI positively correlates with percentage $O^{2-}$. Preferably, two correlations are selected from the foregoing group.

Thus, determining one or more correlations of at least one AF EGM characteristic to a region having ROS-associated cardiac tissue from the plurality of recorded atrial EGMs for the tissue permits the identification of one or more correlations of an AF EGM characteristic with a region suspected of having ROS-associated cardiac tissue and enables one to connect regions of ROS-associated cardiac tissue with ablation lesions (FIG. 1; 1.3).

An examination of EGMs for particular sites following a ROS blockade can identify regions having ROS-associated cardiac tissue. The analysis of the EGM preferably performed in accordance with one or more of the aforementioned analytical subroutines permits assessment of at least one AF EGM characteristic before or after ROS blockade.

An ROS blockade can be effected by treating PLA tissues with known inhibitors of oxidases, such as NADPH oxidase, Mitochondrial ROS, NOS and Xanthine oxidase, among others. Examples of NADPH oxidase inhibitors include Apocynin and diphenylene iodonium, among others. An example of a Mitochondrial ROS inhibitor includes mito-TEMPO, as well as others. Examples of NOS inhibitors include $N^6$-(1-iminoethyl)-1-lysine-dihydrochloride, Aminoguanidine, Hemisulfate, 1400 W, 2-Ethyl-2-thiopseudourea-HBr, L-$N^5$-(1-Iminoethyl)-ornithine-2HCl, L-NAME, and L-NIMMA, among others. Examples of Xanthine oxidase inhibitors include allopurinol, oxypurinol, tisopurine, febuxostat and inositols, among others. Preferred inhibitors for effecting ROS blockade include Apocynin and mito-TEMPO.

The decision is then made to avoid ablation or perform ablation on a given AF substrate based upon whether an outcome of the analysis region includes an EGM having a significant change in at least one EGM characteristic with ROS blockade (FIG. 1; 1.4). If a first outcome of the analysis indicates that the region does not contain a significant change in at least one EGM characteristic with ROS blockade (FIG. 1, "NO" at 1.4), then the first outcome triggers a first decision to avoid ablation of the analysis region (FIG. 1; 1.5). If a second outcome of the analysis indicates that the region contains a significant change in at least one EGM characteristic with ROS blockade (FIG. 1, "YES" at 1.4), then the second outcome triggers a second decision to perform ablation of the analysis region (FIG. 1; 1.6).

Examination of Altered $Ca^{2+}$ Cycling Activity Associated with Sites Having ROS-Associated Cardiac Tissue ROS production results in altered $Ca^{2+}$ cycling (which underlies triggered activity and altered repolarization). In HF induced by rapid RV pacing, $I_{to}$, $I_{Ks}$, $I_{Ca-L}$, and SERCA2a and RyR2 exhibit decreased expression and/or function; while NCX expression and function is increased, and phospholamban (PLB) phosphorylation is increased; and isolated atrial myocytes exhibited signs of $Ca^{2+}$ overload, that is, increased sarcoplasmic reticulum (SR) $Ca^{2+}$ content, increased $Ca^{2+}$ transients, and increased spontaneous $Ca^{2+}$ release (SCR) events and triggered activity. All of the atrial ion-channel and E-C coupling proteins mentioned above can be modulated by ROS. Indeed, the ROS activation of kinases and inactivation of phosphatases is consistent with the well-known aberrant phosphorylation of RyR and PLB in HF. Also, ROS directly decrease SERCA function, but increase NCX function; which parallels the changes in SERCA and NCX in HF. Additionally, ROS increase late/persistent $Na^+$ current ($I_{NaL}$), which is increased in HF. Increased $I_{NaL}$ and 1 forward-mode NCX can significantly contribute to the induction of EADs and DADs. Additional SCR could come from the increased $Ca^{2+}$-sensitivity of hyperphosphorylated RyRs, even if their expression is decreased.

For this reason, AF EGM organization by ROS blockade can be attributed least in part to modulation of $Ca^{2+}$ cycling. In order to further confirm the precise contribution of ROS to the genesis of AF EGMs and ROS 'responsive' EGMs, the $Ca^{2+}$ cycling characteristics of underlying myocardium can be evaluated using optical mapping techniques. The principle is briefly explained here and more fully described in the Examples. The E-C coupling characteristics of the HF and RAP atrium are obtained and compared with the characteristics of overlying AF EGMs. The complex AF EGMs that overlie regions of irregular $Ca^{2+}$ activity (for example, SCR, alternans, ectopic activity) provide important correlations of irregular $Ca^{2+}$ activity with ROS-sensitive AF EGMs.

Computer Implementable Software and Hardware

Some embodiments according to certain aspects of the present invention may be realized in hardware, software, or a combination of hardware and software. Some aspects of some embodiments of the present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

Some embodiments according to some aspects of the present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

Some embodiments according to some aspects of the present invention contemplate one or more processors operatively coupled to one or more memories (for example, a non-transitory computer readable medium) in which one or more steps described herein are stored as instructions or executable code in the one or more memories and are executed by the one or more processors or are used to configure the one or more processors. Some embodiments according to some aspects of the present invention contemplate that the one or more processors and the one or more memories are part of a computer system. The computer system may be part of, for example, laboratory equipment or medical equipment.

Some embodiments according to some aspects of the present invention contemplate that the one or more processors and/or the one or more memories are part of an integrated circuit and/or an application specific integrated circuit (ASIC) and/or a single integrated circuit chip.

Some embodiments according to some aspects of the present invention contemplate using software, hardware and/or firmware.

Some embodiments according to some aspects of the present invention contemplate using a software algorithm that can be installed in commercially available EGM imaging and computer machine language-based analysis stations The software algorithm may compute, for example, correlation functions obtained from one or more of DF, OI, FI, and ShEn analyses of EGM recordings to obtain a decision whether to perform ablation therapy on a selected region. The software algorithm can be realized, for example, in Matlab, C, C++, Pascal, Java, Fortran, Perl, Basic, machine language or other programming languages. To any extent to which specific processing hardware is provided to realize the algorithm, some embodiments according to some aspects of the present invention provide for digital signal processors and/or field programmable gate array, etc. Some embodiments according to some aspects of the present invention also contemplate that a data interface with an existing EGM recording system provide raw data, which includes spectral data directly output from a recorder.

Kits are contemplated with the scope of the present disclosure. Preferred components of kits include algorithm-encoded software on a computer machine readable medium that permits execution of instructions by a machine for implementing the methods of the present invention to guide in the selection of AF substrate for substrate-guided ablation for HF. Kits can also include instructions, manuals, and on-line help sections for assisting users with implementing the executable software code.

Gene Therapeutic Approaches to Reducing ROS-Associated Cardiac Tissues

According to one embodiment, a method of reducing reactive oxygen species-associated (ROS-associated) cardiac tissue in a subject is provided. The method can include several steps. One step is providing an isolated therapeutic DNA. In one aspect, the therapeutic DNA includes a dominant negative TGF-β R2 cDNA expression vector that encodes and expresses dominant negative TGF-β R2 mRNA and protein in vivo. In another aspect, the therapeutic DNA includes a NOX2 shRNA transgene expression vector that encodes and expresses NOX2 shRNA in vivo. A second step includes administering the isolated therapeutic DNA to myocardial tissue of the subject. A third step includes an executing step that includes assessing ROS-associated cardiac tissue status of plurality of recorded atrial EGMs for a region of the myocardial tissue after administration of the therapeutic DNA. A fourth step includes determining a first outcome of executing step and a second outcome of executing step for a region based upon the one or more continued significant changes in EGM characteristics with administration of the therapeutic DNA. The first outcome triggers a first decision to forego therapy of the analysis and the second outcome triggers a second decision to perform therapy of the analysis region of the tissue.

In certain aspects, the method includes analyzing a plurality of recorded atrial EGMs using at least one analytical subroutine selected from the group consisting of dominant frequency analysis (DF), organizational index analysis (OI), fractional interval analysis (FI) and Shannon Entropy analysis (ShEn). In certain aspect, the first outcome consists of no continued significant changes in EGM characteristics following administration of the therapeutic DNA and the second outcome consists of at least one continued significant change in EGM characteristics following administration of the therapeutic DNA. In certain aspect the preferred subject is a patient in need of preventative treatment for stroke or congestive heart failure as a result of atrial fibrillation. In certain aspects, the assessment of no continued significant changes in EGM characteristics is indicative of an increase in ROS-associated cardiac tissue and wherein at least one continued significant change in EGM characteristics is indicative of a reduction in ROS-associated cardiac tissue. In certain aspects, the method can use the myocardial tissue that includes PLA. In certain aspects, the step of administering the isolated therapeutic DNA to myocardial tissue of the subject can include injecting the isolated therapeutic DNA.

EXAMPLES

The invention will be more fully understood upon consideration of the following non-limiting examples, which are offered for purposes of illustration, not limitation.

Example 1

General Methods and Procedures

General methods and procedures for the examples presented below, as well as described elsewhere in the specification, are described in detail in U.S. patent application Ser. No. 13/890,112, filed May 8, 2013 and entitled USING INTRACARDIAC ELECTROGRAMS TO PREDICT LOCATION OF FIBROSIS AND AUTONOMIC NERVES IN THE HEART to Rishi Arora and U.S. patent application Ser. No. 13/890,116, filed May 8, 2013 and entitled Inhibition of Fibrosis and AF by TGF-BETA INHIBITION IN THE POSTERIOR LEFT ATRIUM (PLA) to Rishi Arora, the contents of which are hereby incorporated by reference in their entireties.

Example 2

NADPH Oxidase and Mitochondrial ROS are Major Sources of ROS in the HF and RAP Atrium Ten dogs were subjected to rapid RV pacing at 240/min for 3 weeks. 4 dogs were subjected to rapid RA pacing at 600 bpm for 3-4 weeks. At the end of the pacing period, the atria were removed and snap frozen. PLA tissue was subjected to the lucigenin chemiluminescence assay to assess for $O^{2-}$ (measured per 100 µg of protein) production. The assay was performed as described Kim Y M et al. Circ Res 97:629-36 (2005), the contents of which are hereby incorporated by reference in its entirety. Appropriate inhibitors for each major source of ROS were given in all specimens. NADPH induced $O^{2-}$ was measured in 5 normal dogs. NOX expression in PLAs from all HF dogs was assessed by Western blot.

Figure 2:
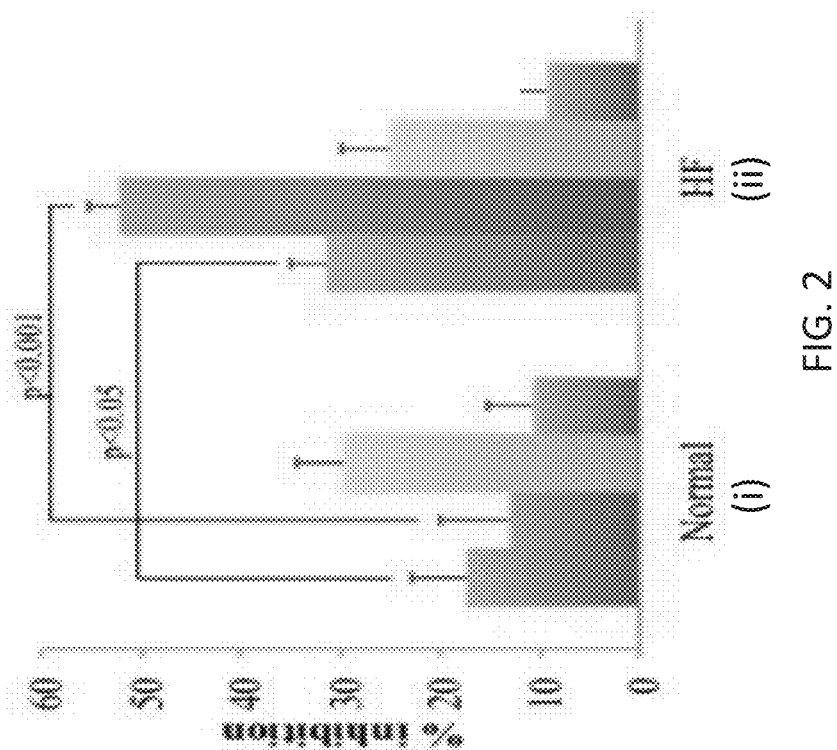
FIG. 2 shows that percent inhibition of $O^{2-}$ generation in animals with normal PLA (subpanel (i)) versus animals with HF PLA (subpanel (ii)) as a function of different inhibitors directed to NADPH oxidase (blue), Mitochondrial ROS (red), NOS (green) and Xanthine oxidase (purple). The differences in percent inhibition of $O^{2-}$ generation between animals having normal PLA vs. HF PLA was statistically significant for sources of $O^{2-}$ generation from NADPH oxidase and Mitochondrial ROS (p values indicated).
Figure 3:
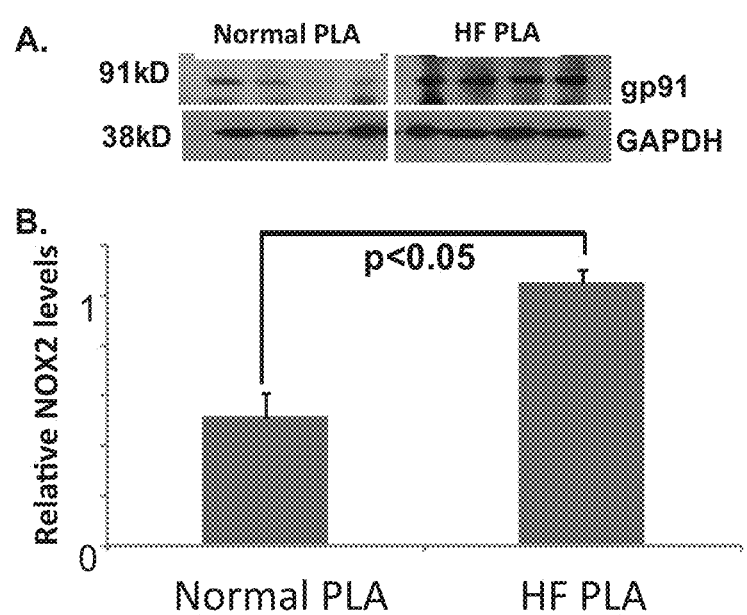
FIG. 3A shows representative blots of NOX2 and GAPDH as loading control for animals with normal PLA and animals with HF PLA.
FIG. 3B shows quantification of the NOX2 in animals having normal PLA versus animal having HF PLA.
Figure 4:
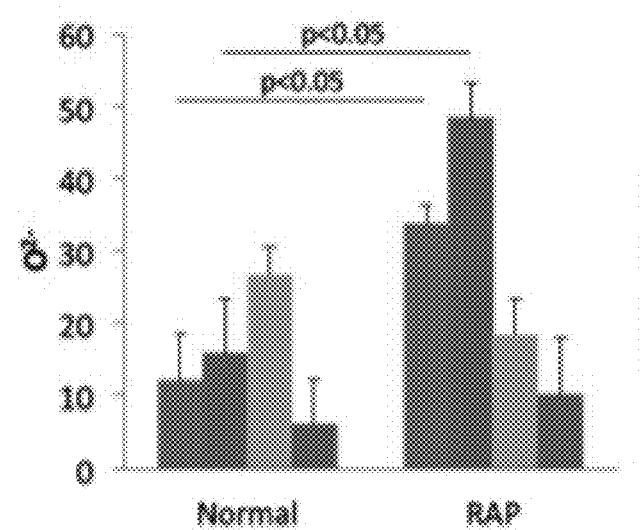
FIG. 4 shows that total $O^{2-}$ production for animals having normal PLA (subpanel (i)) versus animals having rapid atrial pacing (RAP) PLA, as a function of different inhibitors directed to NADPH oxidase (blue), Mitochondrial ROS (red), NOS (green) and Xanthine oxidase (purple). The differences in percent inhibition of $O^{2-}$ generation between animals having normal PLA vs. HF PLA was statistically significant for sources of $O^{2-}$ generation from NADPH oxidase and Mitochondrial ROS (p values indicated).

FIG. 2 shows that total $O^{2-}$ was significantly greater in the HF PLA than in control PLA, with NOX2 and mitochondrial ROS being the two major contributors to total $O^{2-}$ in the HF atrium. Western blot showed NOX2 expression was significantly greater in HF than in normal PLAs. FIG. 3A shows representative blots of NOX2 and GAPDH as loading control; FIG. 3B shows quantification of the NOX2 in normal vs. HF PLA. FIG. 4 shows that total $O^{2-}$ was significantly elevated in the RAP PLA as well, with NOX2 and mitochondrial ROS being major contributors to total $O^{2-}$.

Example 3

Sensitivity of AF EGMs in HF and RAP Model to Acute ROS Blockade

Figure 5:
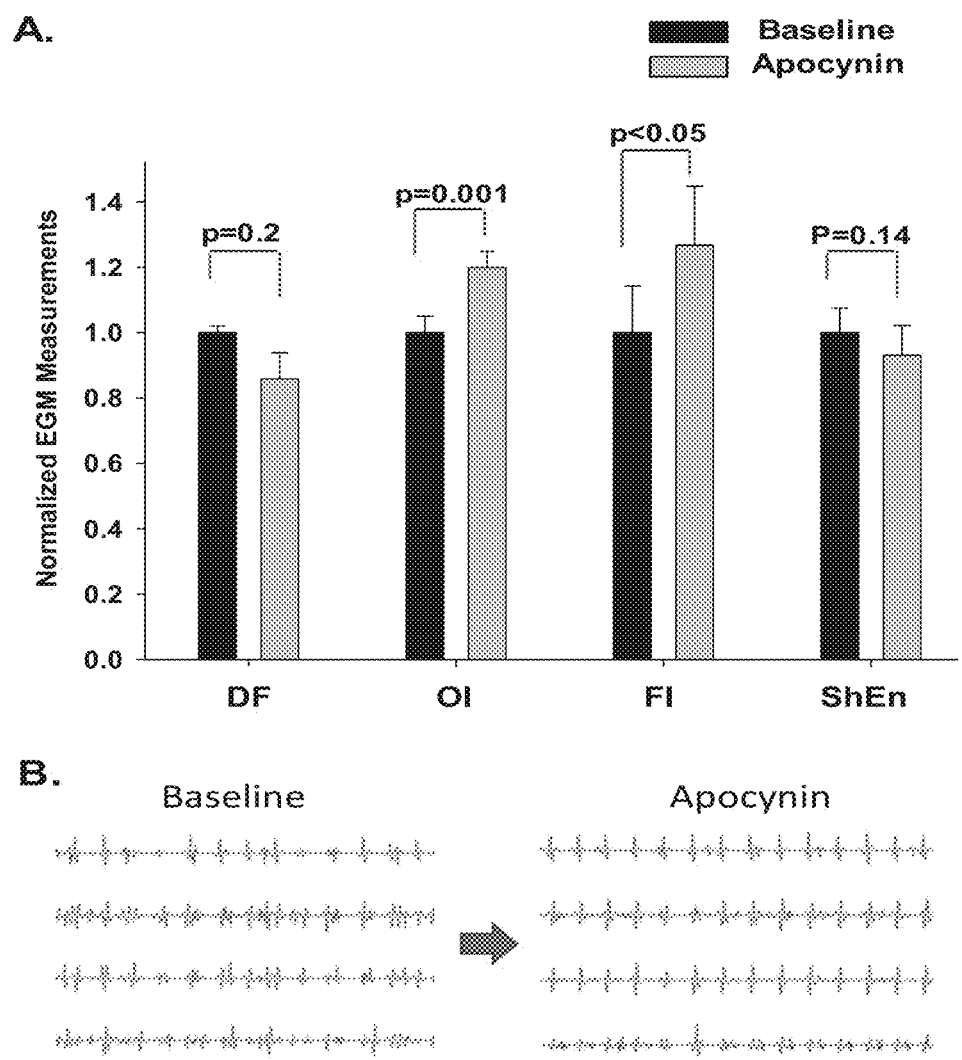
FIG. 5A depicts normalized EGM measurements (DF, OI, FI, ShEn) for animals without treatment (baseline) or following treatment with Apocynin (an NADPH oxidase inhibitor).
FIG. 5B depicts the profile changes in EGM measurements (DF, OI, FI, ShEn [top to bottom]) for animals without treatment (baseline) or following treatment with Apocynin (an NADPH oxidase inhibitor).
Figure 6:
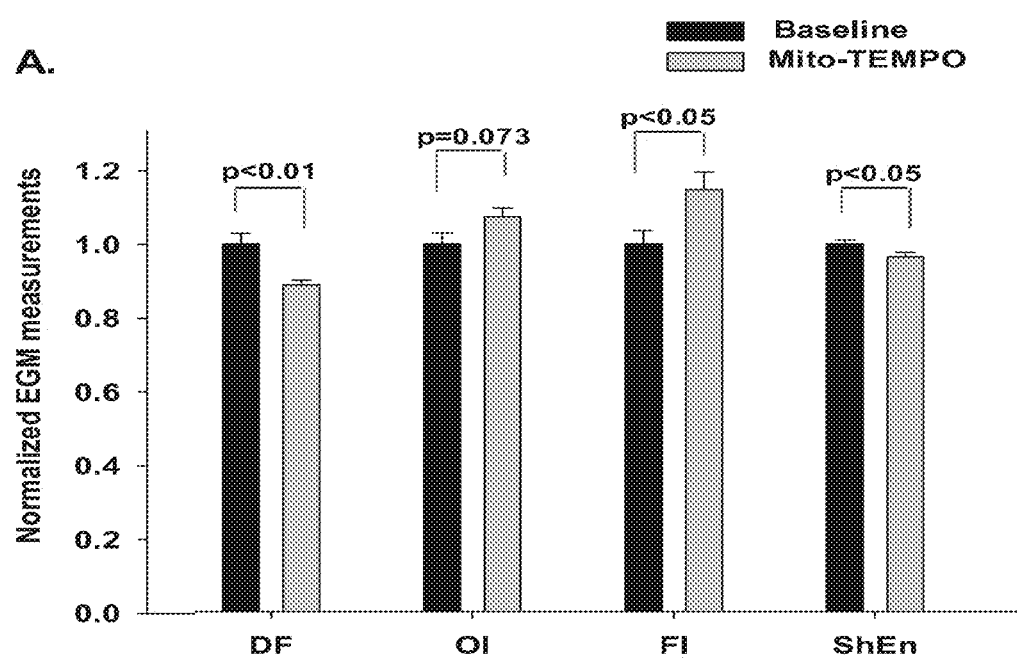
FIG. 6A depicts normalized EGM measurements (DF, OI, FI, ShEn) for animals without treatment (baseline) or following treatment with mito-TEMPO (a Mitochondrial ROS inhibitor).
FIG. 6B depicts normalized EGM measurements (DF, OI, FI, ShEn [top to bottom]) for animals without treatment (baseline) or following treatment with mito-TEMPO (a Mitochondrial ROS inhibitor).
Figure 7:
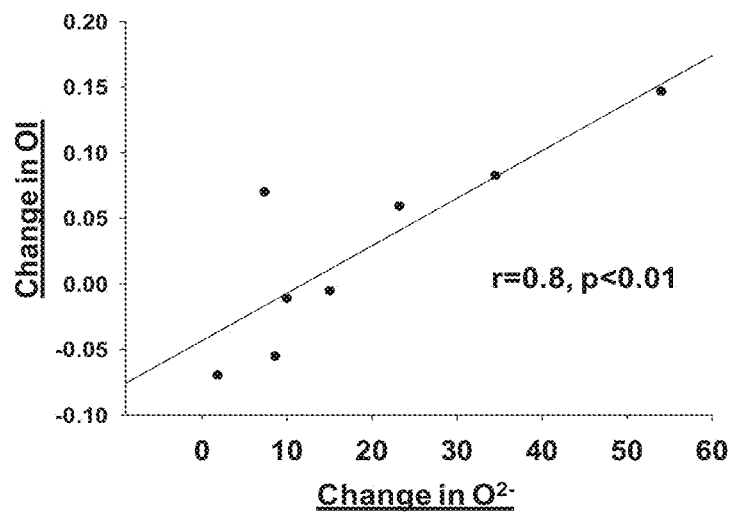
FIG. 7 depicts a plot showing the change in OI as a function of $O^{2-}$ levels in PLA.

HF: In 4 animals, rapid RV pacing was performed at 240 beats/min for 3-4 weeks to induce HF. AF was then induced and AF EGMs recorded by an epicardial, multielectrode plaque (130 electrodes; UNEMAP). Apocynin (an NAPDH oxidase inhibitor) was then given (10 mg/kg) acutely. After apocynin administration, AF slowed and then terminated within 5 minutes (in every experiment). FIG. 5A shows organization of all AF EGM parameters after apocynin administration. FIG. 5B shows an example of slowing and organization of AF EGMs after apocynin administration. After apocynin washout (90 minutes), AF was re-induced and mito-TEMPO was given (0.7 mg/kg). As with apocynin, there was gradual slowing and termination of AF in every animal. FIG. 6A shows organization of all AF EGM parameters after mito-TEMPO administration. FIG. 6B shows an example of slowing and organization of AF EGMs after mito-TEMPO administration. The atrial tissue was then removed and examined for $O^{2-}$ generation using lucigenin chemiluminescence. As shown in FIG. 7, the change in OI with apocynin correlated significantly with the amount of NADPH induced $O^{2-}$ in the respective PLA quadrants. Similarly, the change in DF correlated significantly with $O^{2-}$ levels (r=0.7, p<0.05). Thus, AF EGMs in HF are very sensitive to acute blockade of NADPH oxidase and mitochondrial ROS and AF EGM organization in response to ROS blockade closely correlates with the amount of $O^{2-}$ in underlying tissue.

Figure 8:
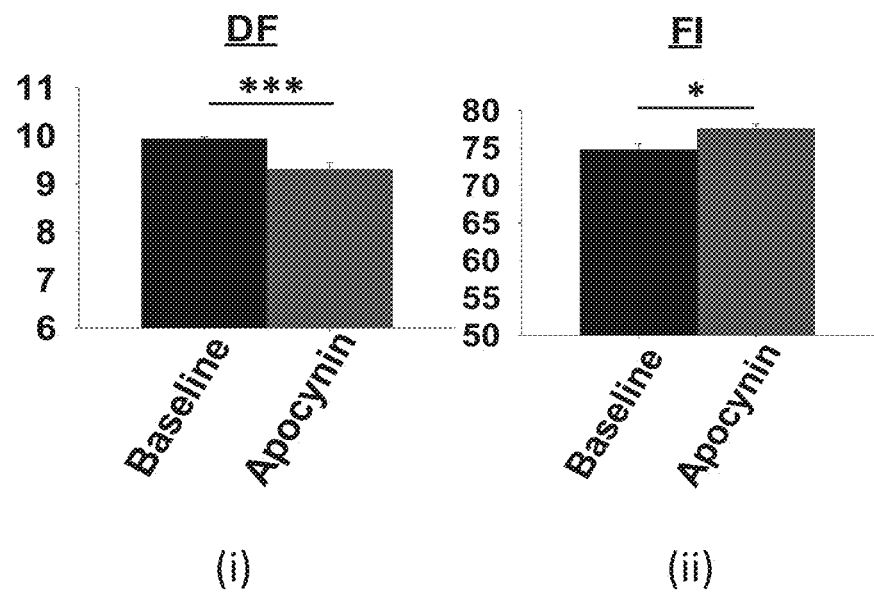
FIG. 8 depicts normalized EGM measurements in animal model of rapid atrial pacing for DF (subpanel (i)) and FI (subpanel (ii)) as a function of absence (baseline) or presence of Apocynin.

RAP: In 2 animals, rapid atrial pacing was performed at 600 bpm for 3-4 weeks to induce persistent AF. Apocynin was given as in HF above. As shown in FIG. 8, apocynin resulted in a significant decrease in DF and increase in OI. In one animal, there was termination of AF with apocynin. These data show that AF EGMs in a RAP model are very sensitive to acute blockade of NADPH oxidase.

Example 4

Simultaneous Voltage ($V_m$) and $Ca^{2+}$ Mapping (Optical Mapping) During Rapid Pacing and During AF (Prophetic Example)

High-Resolution Optical Mapping of Left Atrium:

The animal will be euthanized and the heart (and adjoining PVs) quickly removed. The LA will be Langendorf perfused as previously described by Arora R et al. *Circulation* 107:1816-21 (2003). Optical mapping will then be performed with pacing (for HF dogs only, as these will be in sinus rhythm at baseline; RAP dogs are expected to be in spontaneous AF at baseline) as well as during AF (for both HF and RAP dogs).

Pacing Protocol:

In HF dogs (which will not be in AF at baseline), pacing will then be performed from the mid-PLA with bipolar plunge electrodes (Arora R et al. *Circulation* 107:1816-21 (2003)). A basal (e.g., 1 Hz)—variable rapid (e.g., 2-5 Hz)—pause pacing protocol (Wasserstrom J A et al. *Circ. Res.* 107:1117-26 (2010)) will be used to induce alternans/spontaneous $Ca^{2+}$ release (SCR)/triggered activity.

Figure 9:
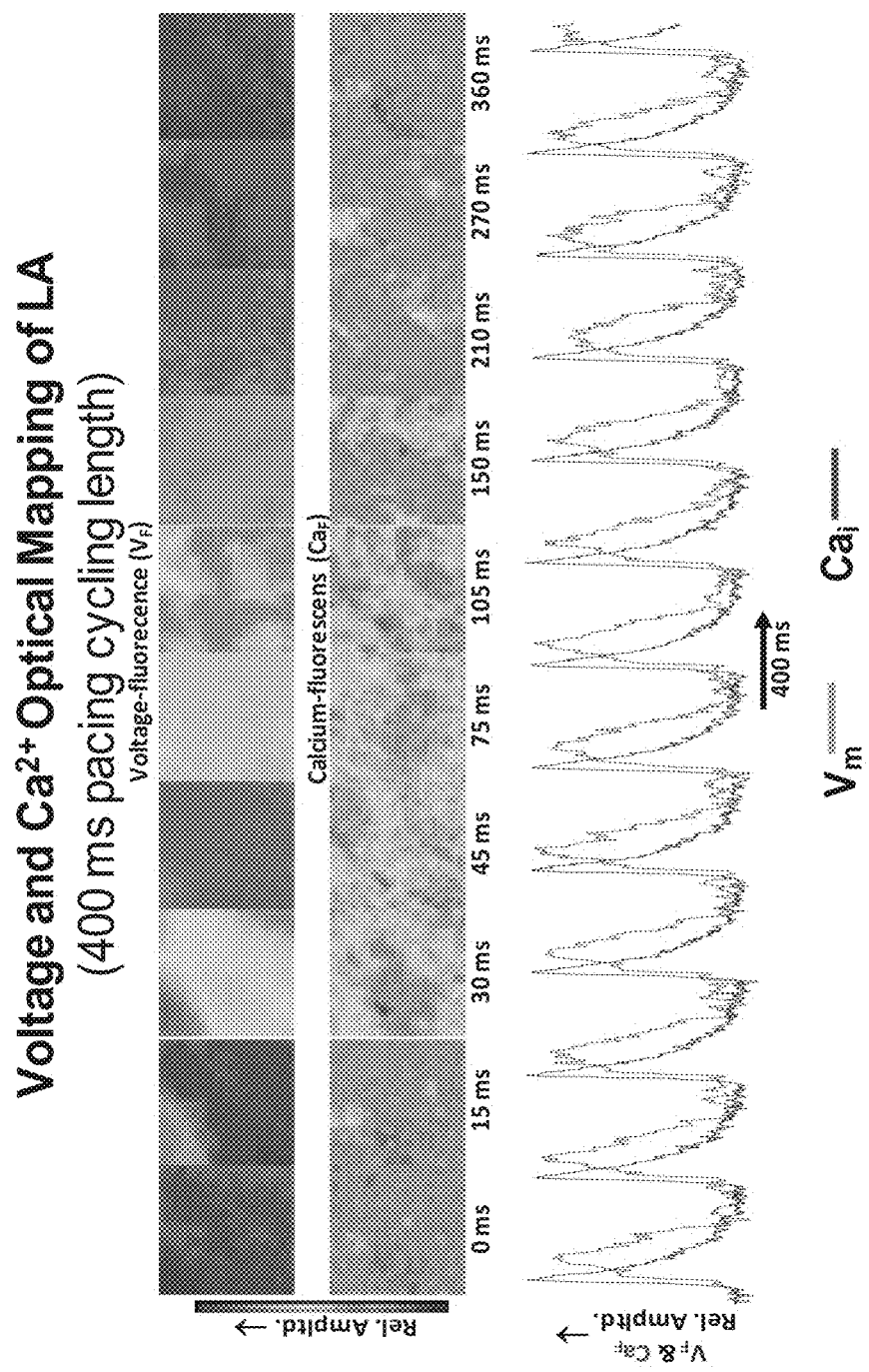
FIG. 9 depicts an example of an optical mapping technique to evaluate altered $Ca^{2+}$ cycling in PLA tissue.

Simultaneous $V_m$ and $Ca^{2+}$ Mapping During Rapid Pacing:

Both transmembrane voltage ($V_m$) as well as $Ca^{2+}$ cycling will be measured simultaneously as previously described (Arora R et al. *Circulation* 107:1816-21 (2003); Efimov I R et al. *Circ. Res.* 95:21-33 (2004); Kong W et al. *Am. J. Physiol. Heart Circ. Physiol.* 302:H1294-305 (2012)). Initial maps will be recorded in the both the PLA and LAA in a 3×3 $cm^2$ field of view, since this field of view is approximately the same size as our contact mapping plaques (see below). Subsequent optical maps will be acquired in the PLA at a higher resolution of 0.5×0.5 $cm^2$. Our optical mapping system consists of an 80×80 pixel CCD camera (Redshirt Imaging) currently attached to optics. An LED light source (green, 300 W) will be used to illuminate the tissue. Changes in $V_m$ and $Ca_i^{2+}$ will be measured with RH237 and Rhod-2AM respectively (Kong W et al. *Am. J. Physiol. Heart Circ. Physiol.* 302:H1294-305 (2012)). For $V_m$ measurements, excitation and emission filters are 530/40 nm and >715 nm respectively. For $Ca_i^{2+}$ measurements, the respective filters are 530/40 nm and 580/40 nm. Emitted fluorescence will measured by the camera at a sampling rate of 2-5 kHz/channel. Cytochalasin D (5 μM) will be added to the perfusate to inhibit contraction. FIG. 9 shows an example of $V_m$ and $Ca_i^{2+}$ signals recorded from Applicant's work from the same region of the canine PLA; the signals were obtained sequentially with a single CCD camera, during atrial pacing at 400 ms.

Simultaneous $V_m$ and $Ca^{2+}$ Mapping During AF:

To be performed in both HF dogs (where AF will be induced by burst atrial pacing) and RAP dogs (which are expected to be in AF at baseline). In HF dogs, after optical mapping during rapid atrial pacing has elucidated sites of alternans/SCR/triggered activity, AF will be induced by rapid (burst) atrial pacing. Using this protocol, we are able to reproducibly induce AF in all our HF dogs. During AF, repeat $V_m$ and $Ca^{2+}$ mapping will be performed. Similarly, simultaneous $V_m$ and $Ca^{2+}$ mapping will be performed during AF in RAP dogs.

Contact Mapping in Explanted Heart:

Following optical mapping, contact mapping will be performed ex-vivo in the Langendorf-perfused atrium using high-density recording plaques. As described above, the initial optical mapping field of view will be approximately the same as the area of the contact mapping plaque. Two 130 electrode plaques are able to fit in the PLA. As described above, optical mapping will be first be performed during sinus rhythm and rapid atrial pacing (for HF dogs; RAP dogs are expected to be in AF at baseline). Optical mapping during AF will be performed for both HF and RAP dogs. After optical mapping has been completed during AF, contact mapping will be performed (during AF) in the same region that had been subjected to optical mapping. The AF signals (EGMs) that have been acquired during ex-vivo contact mapping will be correlated with: a) the results of optical mapping and with b) the results of in-vivo mapping (see Data Analysis below).

Re-Map after IV Apocynin and/or Mito-TEMPO: (N=17 Dogs i.e. 5 Early Stage HF, 7 Advanced HF and 5 RAP):

In some dogs, AF will be recorded after apocynin (10 mg/kg) and/or mito-TEMPO (0.7 mg/kg) administration (in the Langendorf preparation).

Data Analysis:

Optical Mapping:

Analysis will be performed in MATLAB that allows interactive display of raw action potentials and $Ca^{2+}$ transients. Activation and repolarization during pacing and during AF will be analyzed as previously described (Arora R et al. *Circulation* 107:1816-21 (2003); Filgueiras-Rama D, Price N F, Martins R P et al. *Circ. Arrhythm. Electrophysiol.* 5:1160-7 (2012)). $Ca^{2+}$ transients—both stimulated and SCR elicited during rapid pacing—will be studied as previously described (Katra R P et al. *Circ. Res.* 96:535-42 (2005)). The cycle length and frequency characteristics of AF, e.g., DF, as assessed by $V_m$, will be spatially correlated with $Ca^{2+}$ transients recorded during the above-mentioned pacing protocol—both field stimulated as well as SCR events (Katra R P et al. *Circ. Res.* 96:535-42 (2005)). The $V_m$-$Ca^{2+}$ relationship will be assessed at sites that organize with ROS blockade and at sites that do not (organize). Baseline parameters will be compared between ROS sensitive and ROS insensitive EGMs in both the HF and RAP models.

Contact Mapping:

AF EGMs will be assessed using the contact mapping data acquired as described above (to be performed both in-vivo as well as in the explanted heart ex-vivo). AF EGM characteristics (DF, OI, FI, ShEn, RI, $CL_R$) will be spatially correlated with the $V_m$/$Ca^{2+}$ characteristics obtained by optical mapping.

Example 5

Gene-Based Inhibition of ROS Generation in the Atrium i. Transgene to Inhibit TGF-β Signaling—

Figure 10A:
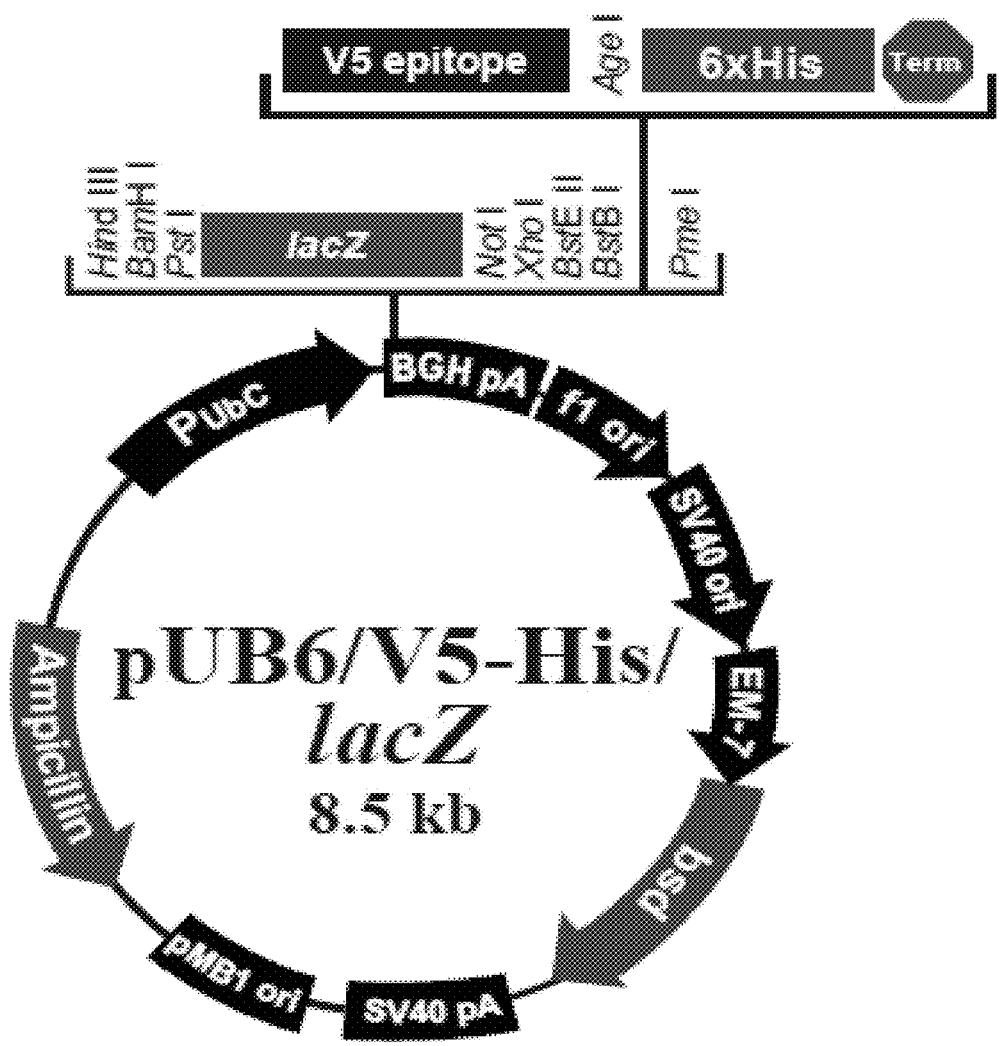
FIG. 10A depicts a control vector (p-UBC-LacZ).
Figure 10B:
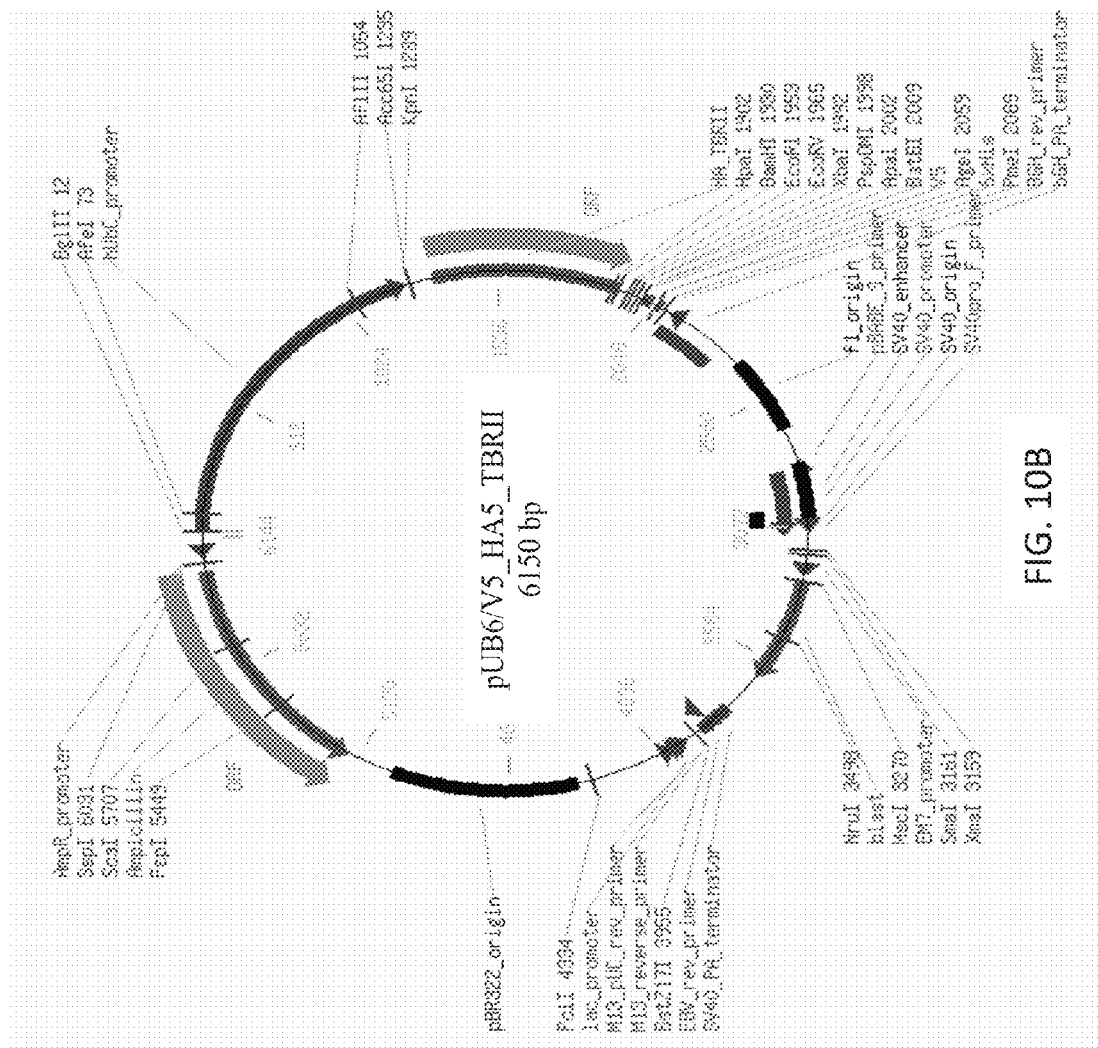
FIG. 10B depicts an expression vector encoding dominant-negative TGF-β type II receptor (pUBC-TGFβdnRII).

Seventeen dogs underwent injection+electroporation in the PLA of either a control vector (p-UBC-LacZ) (FIG. 10A) (N=7), or a plasmid expressing a dominant negative TGF-β type II receptor (pUBC-TGFβdnRII) (FIG. 10B) (N=8), followed by 3-4 weeks of ventricular tachypacing (240 bpm). Pacing is typically begun one week after gene injection. A terminal study was performed to assess for AF inducibility. Tissue was assayed for fibrosis (Trichrome staining) and $O^2$ generation (quantified by lucigenin chemiluminescence). PCR, western blotting and immunohistochemistry were performed to assess for gene expression.

Figure 11:
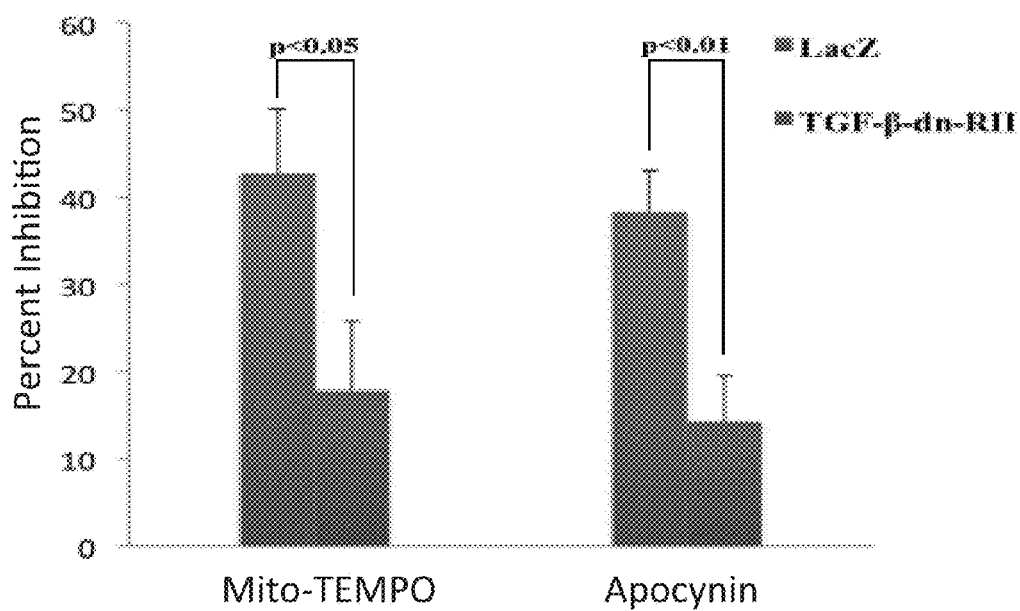
FIG. 11 depicts results of percent inhibition of $O^{2-}$ generation in PLA tissue in animals injected with either a control vector expressing a control protein (lacZ) or a pUBC-TGFβdnRII vector expressing a dominant negative TGF-β type II receptor into the PLA tissue the animals and followed by 3-4 weeks of ventricular tachypacing (240 bpm) of the animals.
Figure 12:
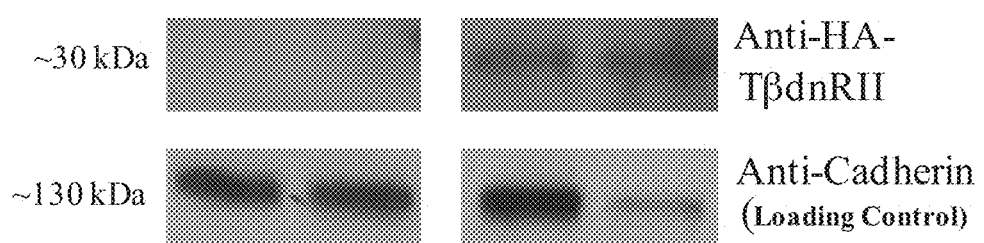
FIG. 12 depicts results of western blotting PLA tissues from animals injected with either control protein (lacZ) or a pUBC-TGFβdnRII vector expressing a dominant negative TGF-β type II receptor into the PLA tissue.
Figure 13:
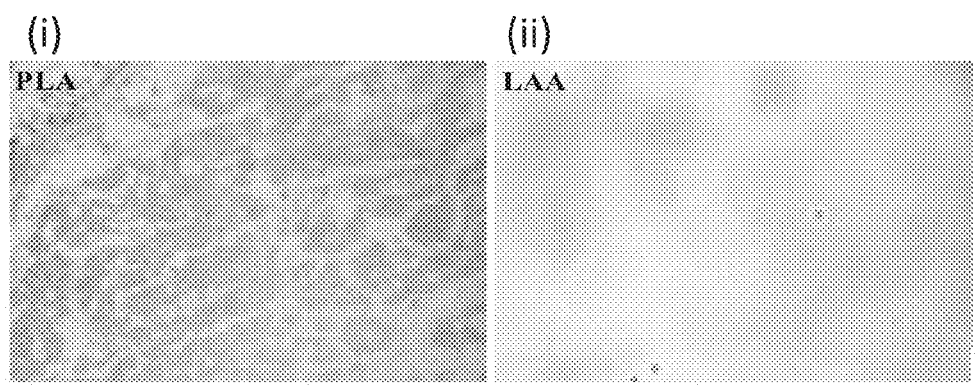
FIG. 13 depicts immunohistochemical staining of PLA and LLA tissues of animals injected with pUBC-TGFβdnRII vector expressing a dominant negative TGF-β type II receptor into the PLA tissue. Subpanel (i): HA tag expressing cells of PLA are stained brown; subpanel (ii): unstained myocytes in the uninjected LAA.

Downregulation of TGF-β signaling by TGFβdnRII significantly attenuated NADPH- and mitochondrial-generated superoxide, as compared to control animals (FIG. 11). FIG. 12 shows robust gene expression in the PLA by western blotting (shows expression of an HA tag in the PLA). FIG. 13 shows that on IHC, gene expression was homogeneous in the PLA (subpanel (i): HA tag expressing cells are stained brown; subpanel (ii): unstained myocytes in the uninjected LAA).

Thus, targeted non-viral gene-therapy approaches aimed at reducing TGF-β signaling in the left atrium results in a decrease in AF substrate, in part through the reduction of oxidative stress. Since pacing was begun one week to 10 days after gene injection, the gene expression data above represents expression around 4-6 weeks after gene injection.

ii. Transgene to Inhibit NADPH Oxidase (NOX2)—

In 2 animals, 5 mg of shRNA against NOX2 (Open Biosystems) under the control of the RNA polymerase III promoter, U6, was injected subepicardially in the PLA, followed by electroporation (to facilitate gene transfer). RV pacing was then performed at 240 bpm for 3 weeks. Open-chest mapping was then performed to assess for AF. The heart was then removed and the LA assessed for gene expression and NADPH stimulated $O^{2-}$ generation (by lucigenin chemiluminescence).

Figure 14:
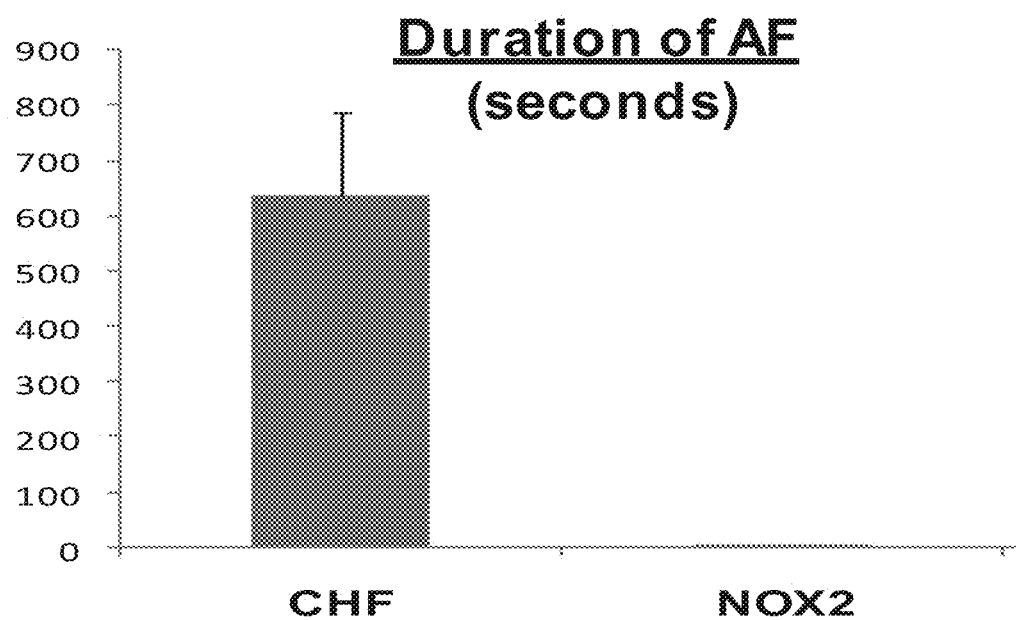
FIG. 14 depicts AF duration in animals having a CHF condition or having been injected with an expression vector expressing a transgene encoding shRNA against NOX2 ("NOX2 shRNA transgene") into PLA tissue.

As shown in FIG. 14, AF duration after 3 weeks of pacing was dramatically less in the NOX dogs than in HF dogs (N=12) that had not undergone gene injection. On real time PCR, 66±17% NOX2 knockdown was noted, as compared to HF PLAs that had not undergone gene injection. NADPH stimulated $O^{2-}$ was also lower in the PLA of these animals as compared PLA of HF controls (25% decrease in NAPDH induced $O^{2-}$ in injected PLA compared to HF controls, and in comparison to un-injected neighboring myocardium).

Example 6

EGM-Guided, Targeted Gene Injection in the Atrium at ROS 'Responsive' Sites

Figure 15:
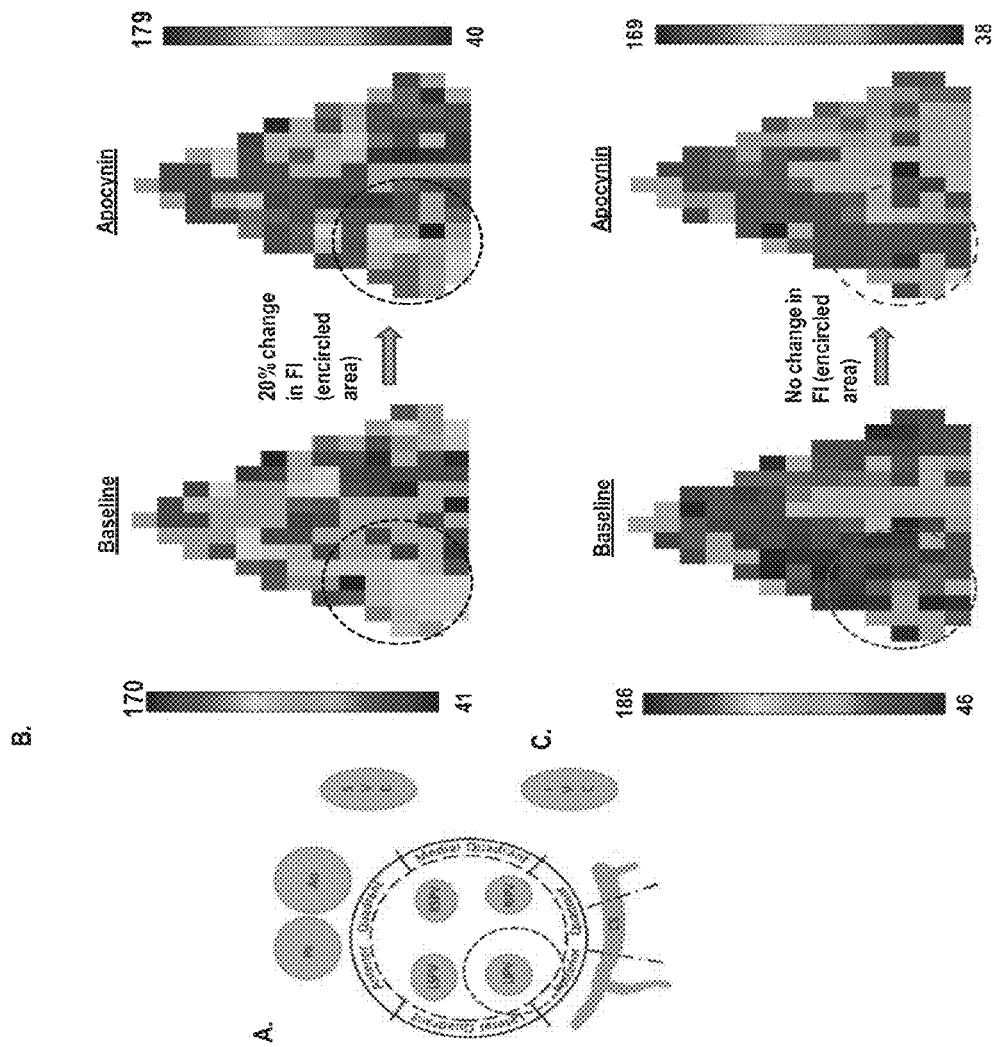
FIG. 15A depicts mapping strategy for EGM-guided gene therapy, wherein the PLA of an animal was divided into 4 equal quadrants for PLA quadrant-specific injection of a NOX2 shRNA transgene and subsequent EGM analysis.
FIG. 15B depicts EGM analysis (FI) in PLA of animals 1 day following injection of the NOX2 shRNA transgene and subsequent treatment in the presence or absence of Apocynin.
FIG. 15C depicts EGM analysis (FI) in PLA of animals 7 days following injection of the NOX2 shRNA transgene and subsequent treatment in the presence or absence of Apocynin.

In one dog, HF was induced by RV pacing at 240 bpm×3 weeks. AF was then induced and recorded in the PLA by high density epicardial plaques (130 electrodes; UNEMAP). Apocynin was given during AF (10 mg/kg); this resulted in organization of AF followed by AF termination. Real time analysis of AF EGMs was performed. The PLA was divided into 4 equal quadrants as shown in FIG. 15A and AF characteristics analyzed for each quadrant. On day 1, injection of NOX2 shRNA was performed in the PLA quadrant that showed the greatest decrease in FI with apocynin (encircled area) (FIG. 15B). One week later, AF mapping was performed again, in the absence and presence of apocynin. As shown in FIG. 15C, on day 7 after gene injection, there was no EGM organization with apocynin in the injected quadrant. NOX2 expression (assessed by RT-PCR) was 70% lower in the injected quadrant than in neighboring, un-injected PLA. Thus, this demonstrates the feasibility of performing targeted gene injection in the atrium at ROS responsive sites.

To the extent that the present application references a number of documents, those references are hereby incorporated by reference herein in their entirety.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The invention claimed is:

1. A method of targeting a region having reactive oxygen species-associated (ROS-associated) cardiac tissue for ablation in a subject, comprising:
   (a) performing at least one EGM analysis of a plurality of recorded atrial EGMs for a site in the region suspected of having ROS-associated cardiac tissue;
   (b) determining one or more correlations of at least one AF EGM characteristic to a region having ROS-associated cardiac tissue from the plurality of recorded atrial EGMs for the site;
   (c) determining a first outcome of executing step (b) and a second outcome of executing step (b) for the site based upon the one or more correlations of at least one AF EGM characteristic to a region having ROS-associated tissue;
   wherein the first outcome triggers a first decision to avoid ablation of the analysis region and the second outcome triggers a second decision to perform ablation of the analysis region of the site;
   wherein the one or more correlations of at least one AF EGM characteristic to a region suspected of having ROS-associated cardiac tissue comprises a further correlation of $Ca^{2+}$ cycling characteristics of underlying myocardium of the site.

2. The method of claim 1, wherein step (a) comprises at least one analytical subroutine selected from the group consisting of dominant frequency analysis (DF), organizational index analysis (OI), fractional interval analysis (FI) and Shannon Entropy analysis (ShEn).

3. The method of claim 1, wherein the subject is a patient in need of preventative treatment for stroke or congestive heart failure as a result of atrial fibrillation.

4. The method of claim 1, further comprising acquiring the plurality of recorded atrial EGMs for the site in a region suspected of having ROS-associated cardiac tissue in real-time from a subject.

5. A method of targeting reactive oxygen species-associated (ROS-associated) cardiac tissue for ablation in a subject, comprising:
   (a) performing at least one EGM analysis of a plurality of recorded atrial EGMs for a site in a region suspected of having ROS-associated cardiac tissue;

(b) assessing the plurality of EGMs before or after ROS blockade;
(c) determining a first outcome of executing step (b) and a second outcome of executing step (b) for the site based upon the one or more significant changes in EGM characteristics with ROS blockade;
wherein the first outcome triggers a first decision to avoid ablation of the analysis region and the second outcome triggers a second decision to perform ablation of the analysis region of the site,
wherein the second outcome of executing step (b) for the site based upon the one or more significant changes in EGM characteristics with ROS blockade comprises a further correlation of $Ca^{2+}$ cycling characteristics of underlying myocardium of the site.

6. The method of claim 5, wherein step (a) comprises at least one analytical subroutine selected from the group consisting of dominant frequency analysis (DF), organizational index analysis (OI), fractional interval analysis (FI) and Shannon Entropy analysis (ShEn).

7. The method of claim 5, wherein the first outcome consists of no significant changes in EGM characteristics with ROS blockade and the second outcome consists of at least one significant change in EGM characteristics with ROS blockade.

8. The method of claim 5, wherein the subject is a patient in need of preventative treatment for stroke or congestive heart failure as a result of atrial fibrillation.

9. The method of claim 5, wherein step (b) is performed with one or more analytical subroutines comprising at least one member selected from the group consisting of DF, OI, FI and ShEn.

10. The method of claim 5, wherein the tissue comprises PLA before or after ROS blockade.

11. The method of claim 5, further comprising acquiring the plurality of recorded atrial EGMs for a tissue in a region suspected of having (ROS-associated) cardiac tissue in real-time from a subject.

* * * * *